United States Patent [19]

Garbe

[11] 4,041,935

[45] Aug. 16, 1977

[54] DEVICE FOR BREATHING MEASUREMENT

[75] Inventor: Dietmar Rudolf Garbe, Maids Moreton, England

[73] Assignee: Vitalograph (Ireland) Limited, Lifford Ennis, Ireland

[21] Appl. No.: 723,958

[22] Filed: Sept. 16, 1976

Related U.S. Application Data

[63] Continuation of Ser. No. 556,014, March 6, 1975, abandoned.

[30] Foreign Application Priority Data

Mar. 7, 1974 United Kingdom ............... 10194/74

[51] Int. Cl.$^2$ ............................................. A61B 5/08
[52] U.S. Cl. .................... 128/2.08; 73/239; 272/99
[58] Field of Search ...................... 128/2.08, 2 C, 209; 272/99; 73/211, 239

[56] References Cited

U.S. PATENT DOCUMENTS

| 3,720,202 | 3/1973 | Cleary | 128/2.08 |
| 3,794,072 | 2/1974 | Diedrich et al. | 128/209 |
| 3,826,247 | 7/1974 | Roskin et al. | 128/2.08 |
| 3,848,585 | 11/1974 | Otsap et al. | 128/2.08 |
| 3,862,628 | 1/1975 | Williams | 128/2.08 |
| 3,871,364 | 3/1975 | Boehringer | 128/2.08 |

Primary Examiner—Robert W. Michell
Assistant Examiner—Lee S. Cohen
Attorney, Agent, or Firm—Bierman & Bierman

[57] ABSTRACT

A device for monitoring the patient's ability to exhale has a piston slidable within a body part by air exhaled through a mouthpiece against a spring. A vent allows part of the air to discharge between the mouthpiece and the piston. By providing one or more discharge openings having removable seals, the amount of air discharged can be set to suit particular circumstances. Advantageously there is provided an indicator movable by, but not returnable with, the piston, to show the maximum position on a scale. The surface of the body part adjacent the scale may be so surfaced as to receive written matter.

7 Claims, 3 Drawing Figures

DEVICE FOR BREATHING MEASUREMENT

This is a continuation of application Ser. No. 556,014 filed Mar. 6, 1975, now abandoned, which claims priority of British Patent application No. 10194/74 dated Mar. 7, 1974.

The present invention relates to devices for breathing measurements and has an object the provision of such a device in a simple form which is convenient for certain applications.

It is well established that useful diagnostic data is obtainable by using a spirometer which indicates the flow pattern of a forced exhalation. A normal spirometer provides a plot of the volume of air exhaled by the patient against time and, from this plot various useful parameters can be derived including the rates of flow at various stages.

An object of the present invention is to provide a simple device by which a rate of flow can be indicated directly.

By the present invention there is provided a device for monitoring a patient's ability to exhale which comprises a hollow body part, a piston member movable therein, a mouthpiece communicating with the interior of the body part for admitting exhaled air to one side of the piston, venting means for permitting discharge of part of the exhaled air from the body part between the mouthpiece and the piston, resilient loading means opposing movement of the piston member through the body part away from the mouthpiece by the pressure of exhaled air on said side of the piston and means for indicating the extent of travel of the piston during an exhalation.

The device of the invention is readily produced in a robust form, capable of being held in the hand is a useful aid to the physician in monitoring changes in a patient's ability to ventilate his lungs when undergoing such treatment as drug and/or inhalation therapy, prescribed breathing exercises, postural drainage and chest percussion. It can be suitable for following changes of the chest condition of a patient without access to a spirometer. In suitable cases it may be carried by the patient himself for collecting comparative data for the physician.

In a preferred arrangement the body part is formed through its wall with a slot running generally in the direction of movement of the piston and the indicating means is movable along the slot by the piston. The indicating means may be attached to the piston. A marker may be provided which is movable along the slot only away from the mouthpiece. Such a marker gives a maximum reading until re-set. It may be provided in addition to the indicating means and, for simplicity, may be movable by the piston acting via the indicating means.

An effective and economic construction is achieved by mounting the piston slidably upon a piston rod within the body part. In this case the resilient loading means may be a helical spring positioned around the piston rod.

By providing the venting means in an adjustable form, the utility of the device can be increased considerably. Adjustment of a single vent can be achieved by providing an adjustable closure therefor, e.g. a slidable or pivotal member mounted on the body part. In a convenient arrangement the venting means comprises a first vent and at least one additional vent provided with a removable seal so that the amount of exhaled air permitted to be discharged from the body part between the mouthpiece and the piston can be increased by the removal of said seal, the device can be adjusted or use with various categories of patients, e.g. the seal or seals can be retained for children, or for adults with restricted breathing, and removed for near-normal adults. Leakage of air past the piston is unimportant provided that the opposite side of the piston is adequately vented and provided, in the case of substantial leakage, that allowance is made therefor in chosing the size of the vent. It is satisfactory to provide the piston in the form of a plate and the body part in the form of a moulding of synthetic resinous material. Some venting is obtainable through a slot as aforesaid.

The device may be provided with a scale, e.g. extending adjcent to a slot as aforesaid, graduated to show the extent of travel of the piston obtained in an exhalation.

Advantageously, the scale is a non-linear one with its divisions occuring more closely as the restoring force of the resilient loading means increases.

Advantageously the body part has at least a part of its surface adapted to be written upon, e.g. suitably roughened when the body part is moulded from synthetic resinous material.

In some applications of the device, the device may be callibrated for the patient by first given an exhalation test upon a conventional spirometer and then a test upon the device itself. The device may then be marked with a standard for the particular case, this being especially convenient if the device has a surface part, adapted to be written upon, provided adjacent to the indicating means.

As will be appreciated, a device of the invention can be useful for comparative measurements and, this being so, it is not essential that the manufacturing tolerances should be such as to provide near-absolute measurements. The scale may be graduated to give readings approximating to standard measurements or it may be graduated in an arbitrary linear or nonlinear manner. A non-linear scale having equal differences between readings falling closer together with distance from the-mouthpiece is normally preferred.

The following description of a preferred embodiment of the device, in which description reference is made to the accompanying drawing, is given in order to illustrate the invention. In the drawing.

A body part C, formed with one open, and one closed, end has its open end fitted with a press-on cap B having a pair of piston stops 1 and a central mouthpiece A. The mouthpiece is of circular cross section throughout. Over the major part of its length it is cylindrical with an internal diameter of 0.5 inch. At its outer end it is tapered over 0.375 inch as shown.

A piston D in the form of a plate profiled to have a loose sliding fit with the body part C has a central hole slidable along a piston rod 2 located by central sockets provided on the cap B and the closed end of the body part C.

Figure 1:
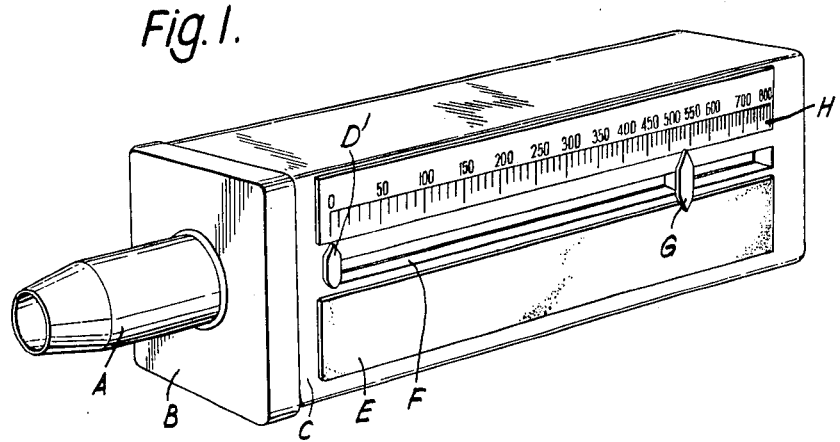
FIG. 1 shows the device in perspective.
Figure 2:
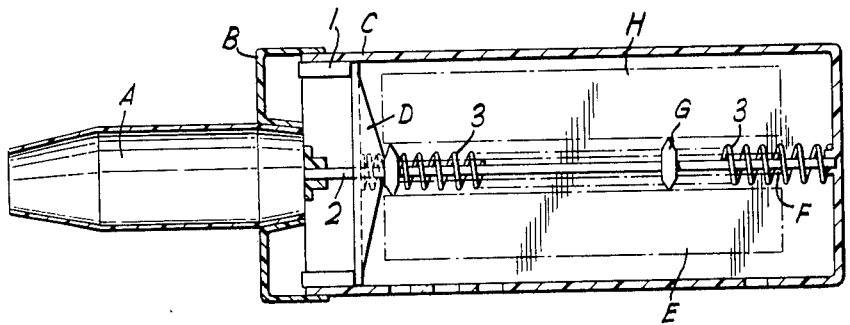
FIG. 2 shows the arrangement of the parts of the device.
Figure 3:
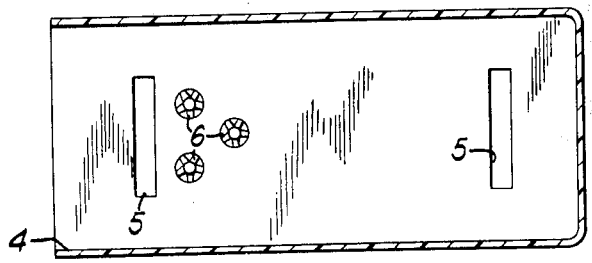
FIG. 3 is a longitudinal cross section through the body part of the device.

An indicator D' integral with the piston passes outwardly through a longitudinal slot F formed through the wall of the body part C and projects to a point adjacent to a scale H on the exterior of the device (FIG. 1). A helical spring 3, fitted over the whole length of the piston rod, normally biases the piston into contact with the stops 1.

Slidably mounted in the slot is a maximum displacement marker G movable in the direction of the closed end of the body part by the indicator D.

The two venting slots 5 are formed in the wall of the body part C as shown in FIG. 5. Three further venting holes 6 provided with removable sealing plugs are provided near the venting slot 5 formed near the mouthpiece end of the body part.

When a patient exhales forcibly through the mouthpiece, the piston D is moved along the piston rod against the resistance of the spring. After the piston has passed the adjacent venting slot, part of the air-flow is discharged to the atmosphere. Because of this venting (supplemented by leakages around the periphery of the piston and around the piston rod vented via the second slot 5 and the slot F) the body part does not have to contain the whole of the exhalation. The movement of the piston against the spring is a function of the rate of exhalation. Marker G moves to indicate the maximum travel of the piston which may be read from scale H.

The properties of the spring and the venting just referred to are arranged so that a reading on the scale is obtained from adult cases of interest, not necessarily from normal healthy adult cases, with the three plugs 6 all removed.

For use with children, or adults having a seriously impaired breathing function, one or more of the venting holes 6 is retained sealed. Adjusting the venting arrangement in this positive incremental way is very satisfactory in that subsequent changes of adjustment are readily noticeable.

A writing surface E, extending along the body part adjacent to the slot F, may be used for marking for the particular patient, a standard reading which may correspond with a parameter known to the physician from a test with a spirometer. Results obtained after are useful for comparative purposes.

1. A device for monitoring a patient's ability to exhale comprising a hollow body part, a piston member having first and second sides, said piston member being moveably mounted in said hollow body part, a mouthpiece mounted to said hollow body part and communicating with the interior of the hollow body part on the first side of the piston member for admitting exhaled air to said first side of the piston member, said piston member being moveable between a first position adjacent the point at which the mouthpiece is mounted to said hollow body part and a second position spaced from said point and determined by the patient's rate of exhalation into said mouthpiece, resilient loading means in the hollow body part and in contact with said piston member for opposing movement of the piston member in the hollow body part away from said mouthpiece by pressure of exhaled air on said first side of the piston member, venting means in said hollow body part for permitting the discharge of part of the exhaled air from the interior of the hollow body part, said venting means being in communication with the interior of the hollow body part on the second side of said piston member when piston member is in said first position and venting the exhaled air to atmosphere only after the piston member passes said venting means as said piston member moves to said second position, said venting means comprising a plurality of individual vents, individual removable seals in said vents for controlling the amount of exhaled air permitted to be discharged from the hollow body part, the amount of exhaled air discharged from said hollow body part being increased by removal of one or more of said individual seals, and means for indicating the extent of travel of the piston member during an exhalation.

2. A device according to claim 1 further comprising a slot in the hollow body part, the slot running generally in the direction of movement of the piston member and the indicating means being mounted in said slot and moveable therein by the piston member.

3. A device according to claim 2 in which the indicating means is attached to the piston member.

4. A device according to claim 2 in which the indicating means is a marker moveable along the slot by the piston member only away from the mouthpiece.

5. A device according to claim 1 further comprising a piston rod in said hollow body part, said piston member being slidably mounted on said piston rod.

6. A device according to claim 5 in which the piston member is in the form of a plate, said plate having an aperture therein, said piston rod passing through said aperture.

7. A device according to claim 1 wherein said indicating means comprises a scale on the exterior surface of the hollow body part graduated to show the extent of travel of the piston member obtained in an exhalation, the hollow body part having an least a part of its surface adjacent the scale adapted to be written upon.

* * * * *